United States Patent [19]

Valcavi

[11] 4,073,938

[45] Feb. 14, 1978

[54] 19,20-BIS-NOR-PROSTENOIC ACIDS AS HYPOLIPEMIC COMPOUNDS

[75] Inventor: Umberto Valcavi, Milan, Italy

[73] Assignees: Istituto Biochimico Italiano di Loredana Lorenzini S.a.s.; Dr. Madaus & Co., both of Milan, Italy

[21] Appl. No.: 600,200

[22] Filed: July 30, 1975

[30] Foreign Application Priority Data

Aug. 7, 1974 Italy ................................. 26111/74

[51] Int. Cl.$^2$ .................. C07C 177/00; A61K 31/215
[52] U.S. Cl. .................................. 424/317; 260/413; 260/511 D; 260/557 R; 260/586 R; 260/617 R; 260/348.46; 260/348.55; 424/305; 560/121; 560/231

[58] Field of Search ............... 260/468 D, 514 D; 424/305, 317

[56] References Cited

FOREIGN PATENT DOCUMENTS 2,316,374    8/1973    Germany ........................... 260/468

OTHER PUBLICATIONS

Valcavi, Il Farmaco, 27, 610, (1972).
Valcavi et al., Il Farmaco, 30, 527, (1675).

*Primary Examiner*—Robert Gerstl
*Attorney, Agent, or Firm*—Hill, Gross, Simpson, Van Santen, Steadman, Chiara & Simpson

[57] ABSTRACT

The invention relates to 19,20-bis-nor-prostanoic acids, and their functional derivatives, endowed with hypolipemic, and antiulcerous properties.

5 Claims, 1 Drawing Figure

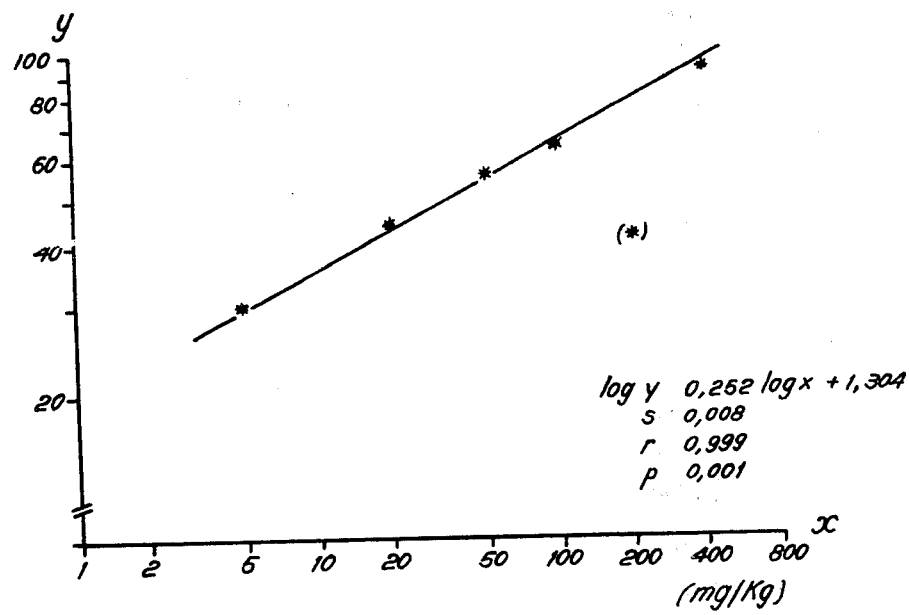

19,20-BIS-NOR-PROSTENOIC ACIDS AS HYPOLIPEMIC COMPOUNDS

Prostaglandins, a group of hormones widely distributed in animal tissue and a group of substances having potent and different pharmacological effects, are known and very well studied from many years.

Some natural or modified prostaglandins are (or will be) useful in human therapy against hypertension, asthma, in the control of fertility and in the induction of parturition.

All natural prostaglandins are derived from prostanoic acid (a cyclopentanonic acid having 20 carbon atoms):

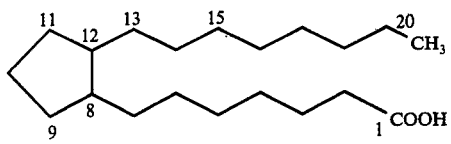

Prostaglandins are biosynthetized from unsaturated $C_{20}$ fatty acids and they have an oxygen function at 9, 11, 15 positions and a double bond in 13 (14) position (Bergström S., Samuelsson B., Ann.Rev.Biochem. 34, 101 (1965);
Bergström S., Advances in the Biosciences: international conference in Prostaglandins, Vienna, September 25–28, 1972 Pergamon Press Vieweg 1973;
Bently P.H., Chem.Soc.Rev. 1973, 24;
Bergström S., Carlson L., Weeks J.R., Pharmacol.Rev. 20, 1 (1968);
Horton E.W., Physiol. Rev. 49, 122 (1969);
Horton E.W., Experientia, 21, 113 (1965);
Chem.Eng.News, October 16, 1972, page 12).

Owing to their high and interesting pharmacological activities, in the recent years, many derivatives of prostaglandins have been synthetized and studied pharmacologically:

| | | |
|---|---|---|
| a) | 11-deoxy prostaglandins | -Caton M.P.L., Tetrah. Letters 1974, 585; -Abraham N.A., Tetrah. letters 1974, 1343; -Lincoln F.H., Schneider W.P., Pike J., J. Org. Chem., 38, 951 (1973); -Crabbe' P., Guzman A., Tetrah. letters, 1972, 115; -Caton M.P.L., Coffee E.C.J., Watkins G.L., Tetrah. letters, 1972, 773; -Sih Ch. J., Salomon R.G., Sood R., Peruzzotti G., Tetrah. letters, 1972, 2435; -Corey E.J., Tetrah. letters 1971, 4753; -Yura Y., Ide J., Chem. Pharm. Bull. 17, 408 (1969); -Neth. pat. 6.612.693 March 9, 1967 (Ayerst); -Bagli J.F., Bogri T., Tetrah. letters, 1967, 5; -Bogri T., Bagli J.F., Deghenghi R., Prostaglandins Proc. Nobel Symposium 2nd, Stockholm 1966, 231; -Bagli J.F., Bogri T., Deghenghi R., Tetrah. letters 1966, 465; Bagli J.F., Tetrah. letters 1969, 1639; -Neth. Appl. 6.611.480, February 17, 1967 (Upjohn Co.); -Hardegger E., Schenk H.P., Broger E., Helv. Chim. Acta, 50, 2501 (1967); -Bagli J., Bogri T., Tetrah. letters, 1972, 3815; -Sakay K., Yura T., Sasaki M., Anemiya S., Yamazaki M. Kohima K., Ger. Offen. 2.147.315 (Sankyo Co. Ltd.); -Abraham N.A., Tetrah. letters 1973, 451; |
| b) | 15-deoxy prostaglandins | -Alvarez F.S., Tetrah. letters 1973, 569; -Pappo R., Collins P.W., Tetrah. letters, 1972, 2627; -Sih Ch. J., Salomon R.G., Price P., Perruzzotti G., Sood R., J. Chem. Soc. Chem. Commun. 1972, 240; |
| c) | allenic prostaglandins | -Crabbe' P., Fried J.H., Ger. Offen. 2.258.668, August 2, 1973 (Syntex Co.); -Crabbe' P., Carpio H., J. Chem. Soc. Chem. Commun. 1972, 904; |
| d) | 9-deoxy prostaglandins | -Caton M.P.L., Tetrah. letters 1972, 3341; |
| e) | 9-keto prostanoic acids | -Sakai K., Ide J., Oda O., Nakumura N., Tetrah. letters 1972, 1287; -Bagli J.F., Bogri T., Ger. Offen. 1.953.232 April 30, 1970 (Ayerst, McKenna and Harrison Ltd.); |
| f) | 8(12)-prostenoic acids | -Attanasi O., Baccolini G., Caglioti L., Rosini G., Gazz. Chim. Ital. 103,31,1973: Miyano M., U.S. Pat. 3.696.144, October 3, 1972 (Searle G.D. and Co.); |
| g) | isomers of pros prostaglandins | -Gandolfi C., Doria G., Gaio P., Ger. Offen. 2.261.496, June 20, 1973 (C. Erba); -Corey E.J. et al. J. Org. Chem. 37, 3043 (1972); -Bagli J.F., Bogri T., Ger. Offen. 1.810.824, July 10, 1969 (Ayerst McKenna and Harrison Ltd.); |
| h) | halogenoderivatives of prostaglandins | -Magerlein B.J., Ger. Offen. 2.320.368, November 15, 1973 (Upjohn Co.); -Crabbe' P., Cervantes A., Tetrah. letters 1973, 1319; |
| i) | chloroprostadienoic acids or cis-5-prosten-13-inoic acids | -Gandolfi C., Doria G., Gaio P., Farmaco ed. sc. 27, 1125 (1972); |
| (l) | 10-oxa-prostaglandins | -Himizu J., Hariyaya S., Ishida A., Yoshikawa K., Sato M., Ger. Offen. 2.229.225, December 21, 1972 (Tanabe Seiyaku Co.); -Haurer F.M., Tetrah. letters 1974, 905; |
| | 9-oxa-15-methyl prostaglandins on the treatment of ulcers | -Lippman W., Seethaler K., Experientia 29, 993 (1973); |
| | 9-oxa-8(12)-prostenoic acids 7-oxa-prostaglandins | -Samuelsson B., Stallberg G., Acta Chim. Scand. 17, 810 (1963); -Fried J., Mehrs M.M., Kao W.L. J. Am. Chem. Soc. 93, 5594 (1971); -Fried J. et al., Prostaglandins Symp. Worcester Found. Exp. Biol. 1967, 351; -Fried J., Tetrah. letters 1970, 2695; |
| m) | methylderivatives of prostaglandins in the treatment of ulcers | -Karim S.M.M., Carter D.C., Bhana D. Ganesan P.A., Prostaglandins 4, 71 (1973); -Guzman A., Crabbe' P., Chem. Ind. 1973, 635; -Bagli J.E., Tetrah. letters 1973, 3329; -Karim S.M.M., Carter D.C., Bhana D., Ganesan P.A., Brit. Med. J., 1973, 143; -Hayashi M., Miyake H., Tanouchi T., Iguchi S., Iguchi Y., Tanouchi F., J. Org. Chem. 38, 1250 (1973); -Bundy G.L., Pike J.E., Ger. Offen. 2.145.600, March 16, 1972 (Upjohn Co.); -Chem. Eng. News, Oct. 2, 1972, page 32; |
| n) | ether of prostaglandins | -Lincoln F.H., Pike J., Youngdale G.A., Ger. Offen. 2.221.443. Nov. 16, 1972 (Upjohn Co.); |
| o) | 10α-hydroxy-prostaglandins | -Crabbe' P., Cervantes A., Meana M.C., J. Chem. Soc. Chem. Commun. 1973, 119; |
| p) | 9,11 bis-deoxy-prostaglandins 11,15-bis-deoxy-prostaglandins | -Crabbe' P., Cervantes A., Guzman A., Tetrah. letters 1972, 1123; -Grieco P.A., Reap J.J., J. Org. Chem. 38, 3413 (1973) and Tetrah. letters 1972, 4083; |
| q) | other substituted prostaglandins | -Bundy G.L., Ger. Offen. 2.154.309, May 4, 1972 (Upjohn Co.); -Schaub R.F., Tetrah. letters 1973, 129; |
| r) | dehydro-prostaglandins | -Miyano M., J. Org. Chem. 35, 2314 (1970); |
| s) | 9,11-bis-homo-prostaglandins | -Harrison J.T., Tetrah. letters 1972, 5151. |

All such above indicated derivatives of prostaglandins have a skeleton of the type:

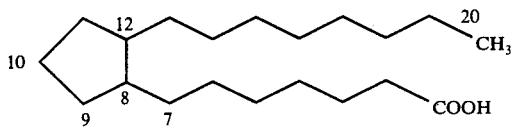

having 20 carbon atoms: optionally one of such carbon atoms is substituted with an oxygen atom (as in oxyprostaglandins) or optionally some substituents like methyl group or halogeno group are introduced in the $C_{20}$ prostanoic acid skeleton.

Only recently few bis-nor-prostanoic acids having 18 carbon atoms (instead of 20 carbon atoms present in all natural and synthetic prostaglandins) have been prepared:

a. the 19,20-bis-nor-9-keto-prostanoic acid methyl ester:

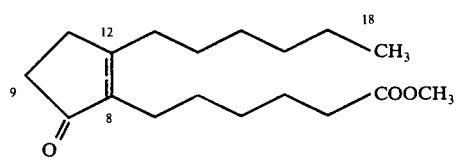

having (or not) a double bond between $C_8$ and $C_{12}$ positions, has been prepared by us (U.Valcavi, Il Farmaco ed.sc. 27, 610 (1972);

b. the compounds having the structure:

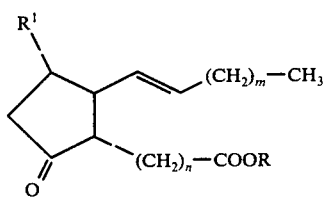

where $R^1$ is H, OH, OOC—$CH_3$; $R^2$ is H, $CH_3$, $C_2H_5$; m is 3, 4, 5; n is 6, 7, have been described by R. Pappo et al. as effective in the treatment of ulcers (Pappo R., Collins P.W. Ger.Offen. 2.305.044 of Aug. 9, 1973, Searle G.D. and Co; R. Pappo, C. Lung Ger.Offen. 2.321.984 of Nov. 15, 1973, Searle G.D. and Co.).

These series of Searle compounds also include the product 19,20-bis-nor-9-keto-13-prostenoic acid (IV) and 19,20-bis-nor-9-keto-11-hydroxy-13-prostenoic acid methyl ester (V):

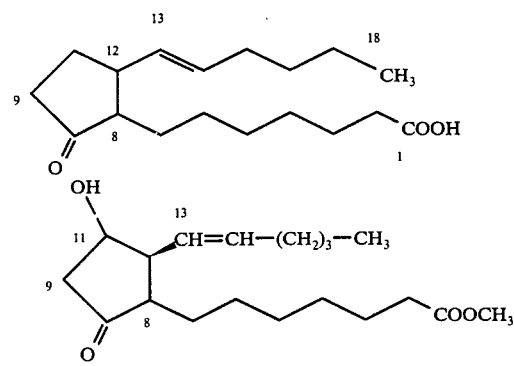

All such Searle compounds have therefore a double bond between $C_{13}$ and $C_{14}$ positions.

Generally, all prostaglandin compounds (including the product of structure III) have been prepared starting from a cyclopentanoic intermediate such as:

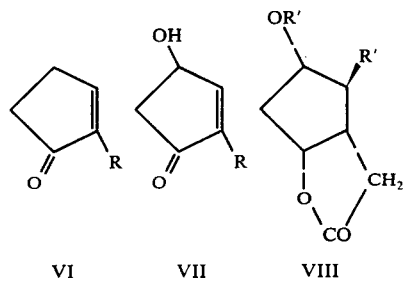

We have now found that:
1. some compounds of the generic formula (IX):

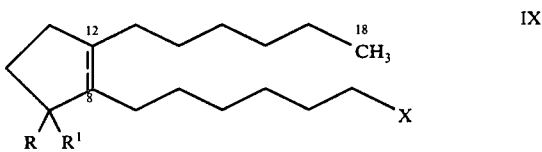

where
R may be H or from $C_1$ to $C_4$ alkyl group;
$R^1$ may be OH, $OR^2$, $NH_2$, $NHR^2$, where $R^2$ is from $C_1$ to $C_4$ alkyl or acyl group;
R and $R^1$ considered together may be on oxygen atom;
where between the $C_8$ and the $C_{12}$ positions there is a double bond; a saturated bond or an oxygen atom (i.e. an oxirane ring);
where
X may be $COOR^3$ ($R^3$ may be H, Na, K, Li, Ca/2, Mg/2, Al/3, an aryl group or $C_1$–$C_4$ alkyl group);
X may be $CH_2OR^4$ (where $R^4$ may be H, from $C_1$ to $C_4$ alkyl or acyl groups);
X may be

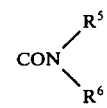

(where $R^5$ and $R^6$ may be H, or from $C_1$ to $C_4$ alkyl group, or together may be part of an heterocyclic ring such as pirrolidine, morpholine, piperidine);
With the clause that, when a ketone group is in position 9 and when positions 8 and 12 are bonded by means of a simple or a double bond, the meaning of X is different from COOH
have interesting hypolipemic, and antiulcerous activities.

For example the compound 9-hydroxy-19,20-bis-nor-prostanoic acid sodium salt (X):

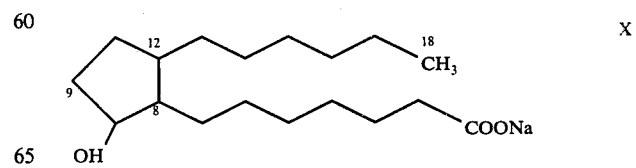

(here named, for brevity, compound $C_{83}$) has the following pharmacological properties:

a. LD50 by mouth in the mouse about 3000 mg/kg
b. Glycemia test at fast: mg/100 ml blood in toto ± E.S.

| controls | 63.8 ± 4.1 | p < 0.001 |
|---|---|---|
| $C_{83}$ | 99.3 ± 2.7 | |

Glycemia test at fast (Repetition): mg/100 ml blood in toto ± E.S.

| controls | 81.1 ± 3.5 | p < 0.01 |
|---|---|---|
| $C_{83}$ | 121.4 ± 9.8 | |

Treatment with the dose of 200 mg/kg endoperitoneal, 2 hours before the test.
Male Sprague-Dawley rats 150 grs.
Groups of 6 animals.
c. Coagulation test: minutes/10 ± E.S.

| | Time of Quick | Time of Howel |
|---|---|---|
| controls | 25.3 ± 0.2 | 84.5 ± 1.6 |
| $C_{83}$ | 29.0 ± 0.4 p < 0.001 | 98.8 ± 0.9 p < 0.001 |

Coagulation test (Repetition): minutes/100 ± E.S.

| | Time of Quick | Time of Howel |
|---|---|---|
| controls | 25.8 ± 0.4 | 95.0 ± 1.5 |
| $C_{83}$ | 29.3 ± 0.3 p < 0.001 | 118.8 ± 2.4 p < 0.001 |

Treatment with the dose of 200 mg/kg endoperitoneal, 2 hours before the test.
Male Sprague-Dawley rate 150 gr.
Groups of 6 animals.

| | | Deepness (mm ± E.S.) | Significativity | Rapidity ± E.S. | Significativity |
|---|---|---|---|---|---|
| controls | | 74.9 ± 6.2 | — | 3.4 ± 0.3 | — |
| aspirin | 2 hours | 48.4 ± 4.4 | p<0.01 | 2.5 ± 0.2 | p<0.05 |
| aspirin | 1 hour | 17.7 ± 2.4 | p<0.001 | 1.2 ± 0.1 | p<0.001 |
| $C_{83}$ | 2 hours | 67.3 ± 12.6 | n.s. | 3.3 ± 0.7 | n.s. |
| $C_{83}$ | 1 hour | 29.1 ± 3.6 | p<0.001 | 1.6 ± 0.2 | p<0.01 |

Treatment with the dose of 200 mg/kg endoperitoneal, one or two hours before sacrifice. Male Sprague-Dawley rats with an average weight of 150 gr.
n.s. = not significative.

| | Triglyceridemia | Cholesterolemia | gr. alcohol/ /rat | Significativity towards | | |
|---|---|---|---|---|---|---|
| | | | | controls | | controls + alcohol |
| | | | | TG | CHOL. | TGCHOL |
| controls | 97.8 ± 5.1 | 91.5 ± 6.6 | | | | |
| alcohol 10% | 169.0 ± 25.0 | 81.0 ± 4.6 | 14.8 | p<0.02 | n.s. | |
| CPIB | 151.2 ± 10.4 | 59.7 ± 2.9 | 16.3 | | | p<0.01 |
| BBA | 143.4 ± 17.8 | 66.5 ± 1.6 | 13.8 | | | p<0.02 |
| $C_{83}$ | 85.2 ± 13.5 | 56.3 ± 3.9 | 12.2 | p<0.02 | | p<0.01 |

Treatment for 1 week CPIB - BBA - 200 mg/kg endoperitoneal; $C_{83}$ 50mg/kg endoperitoneal; only one daily administration.
Male Sprague-Dawley rats 150 gr.
Groups of 6 rats.
CPIB = clofibrate
BBA = β-benzalbutyric acid IBI
n.s. = not significative
TG = triglyceridemia
CHOL. = cholesterolemia

| controls | 58.0 ± 3.3 | |
|---|---|---|
| $C_{83}$ endoperitoneal | 69.7 ± 2.5 | p<0.02 |

| $C_{83}$ by mouth | 71.1 ± 1.9 | p<0.01 |
|---|---|---|

Treatment for 3 days at the dose of 50 mg/kg endoperitoneal or by mouth.
Male Sprague-Dawley rats 150 gr.
Groups of 6 animals.

| | triglycerides | cholesterol |
|---|---|---|
| controls | 96.9 ± 9.4 | 72.6 ± 4.3 |
| Nath diet | 134.9 ± 9.4* | 333.3 ± 29.9** |
| Nath diet + $C_{83}$ endoperitoneal | 91.9 ± 16.3*** | 168.3 ± 26.8**** |
| Nath diet + $C_{83}$ by mouth | 109.4 ± 6.9***** | 380.2 ± 77.8 |

Treatment with 25 mg/kg/die for 1 week on male Sprague-Dawley rats of 150 gr.
Groups of 12 animals.
*p in comparison with controls = <0.02
**p in comparison with controls = <0.001
***p in comparison with Nath diet = <0.05
****p in comparison with Nath diet = <0.001
*****p in comparison with Nath diet = <0.05

| | triglycerides | cholesterol |
|---|---|---|
| controls | 91.1 ± 13.5 | 64.4 ± 2.8 |
| Nath diet | 135.2 ± 22.8 | 180.0 ± 15.8* |
| Nath diet + $C_{83}$ 25 mg | 81.5 ± 13.3 | 108.3 ± 13.9** |
| Nath diet + $C_{83}$ 50 mg | 49.1 ± 6.1*** | 101.8 ± 4.4**** |

Treatment with 25 and 50 mg/kg/die endoperitoneal for 1 week on male Sprague-Dawley rats of 150 gr.
Groups of 12 animals.
*p in comparison with controls = <0.001p in comparison with Nath diet = <0.01*p in comparison with Nath diet = <0.01****p in comparison with Nath diet = <0.001 h. General pharmacology

The compound $C_{83}$ has been tested pharmacologically in order to show a probable prostaglandino-similar activity.

The compound $C_{83}$ has been studied on the above parameters:
1. Trachea of guinea-pig.
2. Strips of fundal end stomach of rat.
3. Uterus of rat.
4. Portal vein of rat.
5. Cardiovascular effects.

This compound has been tested at the concentration of 100 µg/ml in all preparations above mentioned.

The compound $C_{83}$ seems to have a clear prolonged action on muscle on the different kinds of smooth musculature.

i. Anti-ulcerous activity - 9-keto-19,20-bis-nor-8(12)-prostenoic acid, sodium salt

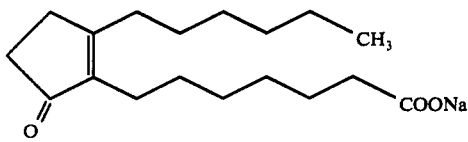

The anti-ulcerous activity of the compound in question is tested on an ulcer induced by aspirin and on an ulcer induced by phenyl butazone. In both models the mucous lesions are localized in the glandular section of the stomach.

I. Ulcer from aspirin

Test animals

Female rats of the Wistar stock weighing 150–175 g were selected. 24 hours before the start of the test the animals were made to fast, allowing water at will.

Method

Each test group consists of 12 animals. The aspirin is administered orally in the form of a suspension (45 mg in ml of 0.5% carboxymethylcellulose for each animal). The application of the sodium salt in question takes place either intravenously (2 × 5 mg or 1 × 50 mg of substance/kg in 2 ml of 0.9% sodium chloride solution) or orally (2 × 10 mg or 2 × 100 mg of substance/kg in 2 ml of 0.5% carboxymethylcellulose suspension). The first dose is administered 10 minutes before application of the aspirin, and the second dose two and a half hours afterwards. The animals are killed 5 hours after the application of the aspirin, and the second dose 2½ hours afterwards. The animals are killed 5 hours after application of the aspirin, the stomachs are prepared, and the number and size of the lesions is evaluated with a stereomicroscope.

Results

The results are summarized in the following table:

| Mode of administration | Dose (mg/kg) | Ulcer scale (x ± Sx) |
|---|---|---|
| p.o. | Controls | 17.95 ± 2.98 |
| p.o. | 2 × 10 | 9.25 ± 2.11* |
| p.o. | 2 × 100 | 5.83 ± 2.11** |
| i.v. | 2 × 5 | 11.80 ± 5.1 |
| i.v. | 1 × 50 | 5.08 ± 2.38** |

*<0.05
**<0.01

The substance in question inhibits considerably the ulcerating effect of the aspirin in both oral doses, and in the higher doses in the case of intravenous application.

II. Ulcer from phenylbutazone

Test animals

Female rats of the Wistar stock weighing 140–170 g are involved. 24 hours before the start of the test the rats are made to fast, while they are allowed water at will.

Method

Each test group consists of 12 animals. For the formation of the ulcer, 200 mg of phenylbutazone/kg in 2 ml of 0.5% gum arabic are administered to the animals orally. 10 minutes before administration of phenylbutazone, and 2½ hours afterwards, substance in question is administered orally (in 0.5% gum arabic solution) or intravenously (in 0.9% sodium chloride solution) in variable doses (see table). The animals are killed 5 hours after administration of phenylbutazone, the stomachs are prepared and examined under a stereomicroscope, to evaluate the number and size of the lesions.

From the Table it results that the compound in question can inhibit the ulcerating effect of phenylbutazone depending on the doses (orally).

Results

| Mode of administration | Dose (mg/kg) | Ulcer scale (x ± Sx) | Inhibition % |
|---|---|---|---|
| p.o. | Controls | 9.25 ± 1.81 | |
| p.o. | 2 × 10 | 4.17 ± 0.91* | 54.9 |
| p.o. | 2 × 100 | 1.83 ± 0.69** | 80.2 |
| i.v. | Controls | 11.17 ± 2.77 | 83.1 |
| i.v. | 2 × 5 | 3.00 ± 0.92* | 83.1 |
| i.v. | 1 × 50 | 6.42 ± 3.41 | 42.5 |

*p<0.05
**p<0.01

1. Anti-ulcerous activity - 9-hydroxy-19,20-bis-nor-prostanoic acid, sodium salt.

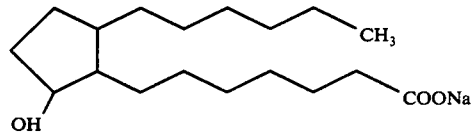

Also in this case the anti-ulcerous activity is tested on an ulcer induced by aspirin and by phenylbutazone. In both cases lesions of various sizes are formed in the glandular section of the stomach.

I. Ulcer from aspirin

Test animals

Female rats of the Wistar stock weighing 150–175 g are used. 24 hours before the start of the test the animals are made to fast, while they are allowed water at will.

Method

Each test group consists of 12 animals. The aspirin is administered orally as a suspension (45 mg/ml of 0.5% carboxymethyl cellulose suspension, 1 ml per animal). The substance in question is administered 10 minutes before the administration of aspirin, and 2½ hours after, each time in doses of distilled water, respectively of 100 mg/kg × 10 ml of distilled water. The animals are killed 5 hours after the administration of aspirin, the stomachs are extracted and with a stereomicroscope the number and size of the lesions is evaluated.

Results

The results are summarized in the following Table:

| Dose (mg/kg) | Ulcer scale (x ± Sx) |
|---|---|
| Controls | 18.67 ± 3.11 |
| 2 × 10 | 4.83 ± 1.09** |
| 2 × 100 | 8.92 ± 1.91* |

*p<0.05
**p<0.001

In both doses the substance in question considerably mitigates the ulcerating effect of aspirin.

II. Ulcer from phenylbutazone

Test animals

Female rats of the Wistar stock weighing 170 ± 180 g are again involved. The animals are held in constant ambient conditions for at least 2 weeks before the start of the test. 24 hours before the start of the test the animals are made to fast, while they are allowed water at will.

Method

Each test group consists of 10 animals. The substance in question is administered a first time 15 minutes before administration of phenylbutazone (200 mg/kg × 1 ml in 0.5% tragacanth gum solution orally), and a second time 2½ hours after. The doses of the substance in question amount to 2.5, 10, 50, 100, 200 and respectively 400 mg/kg × 2 ml of 0.5% tragacanth gum solution, orally.

5 hours after the administration of phenylbutazone the animals are killed, the stomachs are extracted, fixed and with the aid of a stereomicroscope magnifying 8 times a point count evaluation is carried out. The lesions of the gastric mucosa are expressed in % of the stomach surface.

Results

The following Table lists the results of the evaluation referred to the surface:

| Dose (mg/kg) | Surface area of the ulcer in % with respect to surface area of the stomach (x ± Sx) |
|---|---|
| 2 × 2.5 | 0.57 ± 2.10 |
| Controls | 0.80 ± 3.26 |
| 2 × 25 | 0.33 ± 1.59 |
| 2 × 10 | 2.13 ± 2.22 |
| Controls | 3.60 ± 3.33 |
| 2 × 100 | 1.97 ± 1.44 |
| 2 × 50 | 1.30 ± 1.74 |
| Controls | 3.57 ± 3.59 |
| 2 × 200 | 0.27 ± 0.53* |

*p<0.02

If the inhibiting effect of the sodium salt of 9-hydroxy-19,20-bis-nor-prostanoic acid is calculated from the above data, a highly significant correlation between the dose and the inhibition of the surface area of the ulcer is obtained (see FIG. 1), where on the axis of abscissas there is the dose (mg/kg) and on the axis of ordinates there is the percent inhibition of the surface area of the ulcer).

The $D_{E'50}$ is calculated from the regression lines as 37 mg/kg.

2. The compound of generic formula (IX):

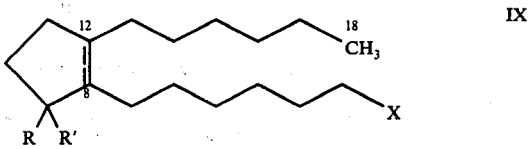

where R, R', X have the same above indicated meaning (see point (1) are prepared starting from easily and economically available $C_{18}$ fatty acids like ricinoleic acid (XI)

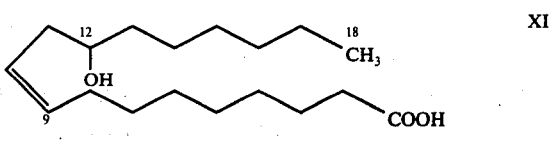

through the following sequence (as in part described in our paper U. Valcavi, Il Farmaco ed.sc. 27, 610 (1972):

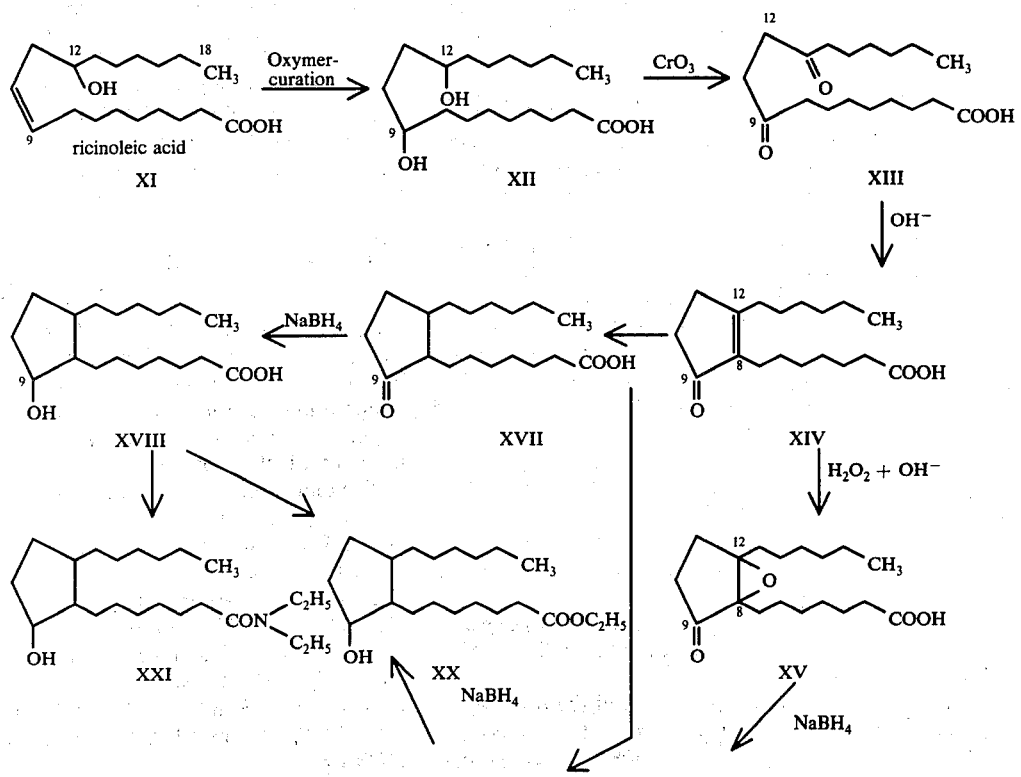

-continued

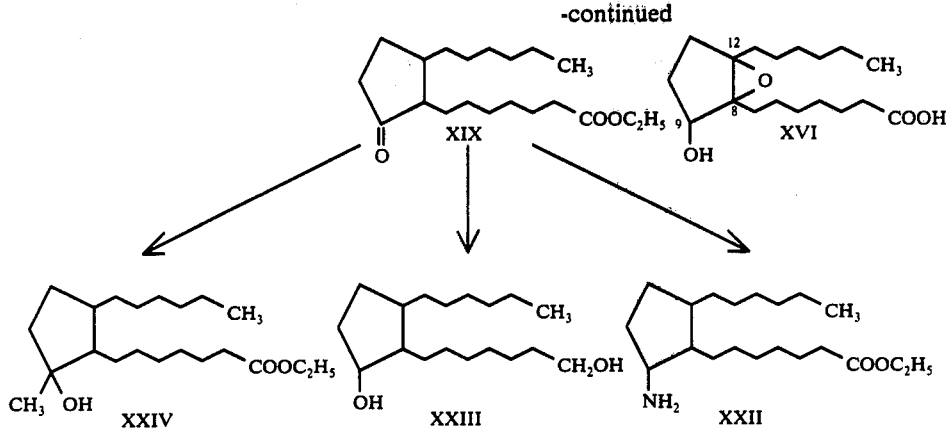

Therefore, 19,20-bis-nor-prostanoic acids, like XIV-XXIV, are easily prepared starting from fatty acids and without using the cyclopentanonic intermediates as VI, VIII which are not so easily available.

The following examples are to be intended as explicative and not limitative.

EXAMPLE 1 : 9,12-hydroxyoctadecanoic acid (XII)

To 534 gr of mercuric acetate, dissolved in 1670 ml of distilled water, 1670 ml of tetrahydrofuran and then 500 gr of ricinoleic acid (9-hydroxy-octadecanoic acid) are added. The mixture is stirred 40 minutes at 20° C, then 1670 ml of NaOH 3N in water and 66.8 gr of NaOH dissolved in 100 ml of water are added at +20°/+25° C.

31.7 gr of NaBH$_4$ dissolved in 1670 ml of NaOH 3N in water are added in 15 minutes at 20/25° C.

The mixture is stirred 10–20 minutes at 20° C, filtered on decalite; the limpid filtrate is acidified to pH 2 with HCl, extracted 3 × 3000 ml of CH$_2$Cl$_2$. The organic phase is washed with water, dried on Na$_2$SO$_4$, evaporated and the residue is crystallized with isopropyl ether; 181.3 gr of compound XII are obtained, m.p. 78°–82°, equivalent weight found 316, I.R. bands at 3200, 1695, 1460, 1410 1375 cm$^{-1}$, no absorption in U.V.

EXAMPLE 2 : 9,12-diketo-octadecanoic acid (XIII)

120 gr of compound XII dissolved in 19.6 lt of acetone are treated at 0° C with 640 ml of solution obtained from 143 gr of CrO$_3$, 284 ml of water and 147 ml of H$_2$SO$_4$ and water to 640 ml.

The suspension is stirred 30 minutes at +10°, filtered; the acetone is removed in vacuo, and the residue is dissolved in 6 lt of CHCl$_3$, washed with water. The solvent is removed in vacuo, and the residue is crystallized with isopropylether giving 82 g of compound (XIII), m.p. 94°–96°, equivalent weight found 304, I.R. bands at 3400, 1720, 1705, 1695, no absorption in U.V., no reaction with FeCl$_3$.

EXAMPLE 3 : 9-keto-19,20-bis-nor-8(12)-prostenoic acid (XIV)

180 gr of 9,12-diketo-octadecanoic acid (XIII) dissolved in 8.5 lt of ethanol 95% are refluxed 4 hours with 8.5 lt of NaOH 4% in water.

The solvent is evaporated in vacuo, the residue is diluted with water, acidified to pH 2 with HCl at +5°, extracted with CHCl$_3$.

The solvent is evaporated in vacuo and the residue is distilled at 0.14 mm of residual pressure: boiling point 240°, $\lambda_{max}^{MeOH}$ 239–240 m$\mu$ $E_{1cm}^{1\%}$ 508 ($\epsilon$ = 15,000), equivalent weight found 292, I.R. bands at 3400, 1735, 1700, 1670, 1625 cm$^{-1}$.

EXAMPLE 4 :
9-keto-8(12)-epoxy-19,20-bis-nor-prostanoic acid (XV)

35 gr of 9-keto-19,20-bis-nor-8(12)-prostenoic acid (XIV) dissolved in 2100 ml of methanol are treated in 10 minutes at 10° with 175 ml of NaOH 4N in water and 238 ml of H$_2$O$_2$ 30% in water.

After 2 hours at room temperature the U.V. absorption of the compound XIV is completely disappeared.

The methanol is evaporated in vacuo to 500 ml, the solution is acidified at 10° with HCl to pH 2, diluted with water, extracted with ethyl ether. The organic phase is washed with water, the solvent is evaporated and 36.9 gr of compound XV are obtained, equivalent weight found 300, no U.V. absorption, I.R. bands at 3400, 3100, 1785, 1735, 1710, 1460, 1406, 1280, 1185, 920 cm$^{-1}$. 29 gr of compound XV are dissolved in 600 ml of water with NaOH to pH 9. The solution is filtered and lyophilized. It has been obtained 29 gr of the sodium salt as white solid product, humidity (K.F.) 1.71%, I.R. bands at 3400, 3200, 1720, 1710, 1560, 1460, 1445, 1375 cm$^{-1}$.

EXAMPLE 5 : 9-hydroxy-8(12)-epoxy-19,20-bis-nor prostanoic acid (XVI)

31 gr of 9-keto-8(12)-epoxy-19,20-bis-nor prostanoic acid (XV) dissolved in 310 ml of methanol are treated at 0° with 19.2 gr of NaBH$_4$; the solution is stirred at room temperature 20 hours. The methanol is evaporated in vacuo, the residue is dissolved in 600 ml of water, treated with 50 ml of acetic acid, extracted with CHCl$_3$.

The chloroform is washed with water, dried on Na$_2$SO$_4$, evaporated in vacuo : 27.1 gr of (XVI) are obtained, I.R. bands at 3410, 1770, 1700, 1460, 1410, 1375, 1200, 1075, 1020, 955, 930, 800, 750 cm$^{-1}$.

25 gr of XVI are dissolved in 400 ml of water with NaOH 15% to pH 9, filtered and lyophilized : 24 gr of sodium salt of XVI as a white solid are obtained, humidity (K. Fisher) 2.08%, no U.V. absorption, equivalent weight found 301.7, I.R. bands at 3400, 1765, 1565, 1460, 1420, 1378 cm$^{-1}$. LD50 by mouth in mice about 1500 mg/kg.

EXAMPLE 6 : 9-keto-19,20-bis-nor-prostanoic acid (XVII) 100 gr of 9-keto-19,20-bis-nor-8(12)-prostenoic acid (XIV) dissolved in 1750 ml of acetic acid are hydrogenated with 17.6 gr of $PtO_2$ and hydrogen at 20° and 1 atm. of pressure. The theoretical amount of hydrogen is absorbed in about 1 hour.

The suspension is then filtered, evaporated in vacuo, diluted with 1000 ml of $CHCl_3$, washed with water. The solvent is removed in vacuo: 93.8 gr of compound XVII are obtained as an oil, no U.V. absorption, I.R. bands at 3400, 3000, 1740, 1700 $cm^{-1}$.

EXAMPLE 7 : 9-hydroxy-19,20-bis-nor-prostanoic acid (XVIII)

68 gr of 9-keto-19,20-bis-nor-prostanoic acid (XVII) dissolved in 660 ml of methanol are treated at 0° with 52 gr of $NaBH_4$.

After 20 hours at 20°, the solvent is evaporated in vacuo, the residue is dissolved in 1300 ml of water treated with 120 ml of acetic acid, extracted with chloroform. After solvent evaporation, 65.1 gr of the compound XVIII are obtained, as an oil, I.R. bands at 3420, 3100, 1710 $cm^{-1}$. 35 gr of the compound XVIII are dissolved in 600 ml of water with NaOH to pH 9. The solution is filtered and lyophilized: 35.5 gr of sodium salt of 9-hydroxy-19,20-bis-nor-prostanoic acid are obtained, as white solid, humidity (K.Fisher) 1.73%, no U.V. absorption, equivalent weight found 320, I.R. bands at 3400, 3300, 1565, 1460, 1390 $cm^{-1}$, LD50 by mouth in mice about 3000 mg/kg.

EXAMPLE 8 : 9-keto-19,20-bis-nor-prostanoic acid ethyl ether (XIX)

15 gr of 9-keto-19,20-bis-nor-prostanoic acid (XVII) dissolved in 70.5 ml of ethanol 99%, are refluxed with 5.28 ml of $H_2SO_4$ 6 hours.

The ethanol is evaporated in vacuo, 220 ml of water are added. The suspension is extracted with $CHCl_3$, the organic phase is washed with water, $NaHCO_3$ 5% in water, water again and the solvent is removed in vacuo: the residue is distilled at 0.017 mm of residual pressure at 150°-160°, gr. 13, I.R. bands at 1735, 1700, 1460, 1370, 1250, 1180, 1100, 1030, 855, 725 $cm^{-1}$.

EXAMPLE 9 : 9-hydroxy-19,20-bis-nor-prostanoic acid ethyl ester (XX)

a. starting from XIX 12 gr of compound XIX dissolved in 115 ml of methanol are treated at 0° with 9.3 gr of $NaBH_4$, the solution is stirred at room temperature for 20 hours. The solvent is removed in vacuo, 230 ml of water are added and the product is extracted with chloroform.

After evaporation of the solvent, 11.8 gr of the compound XX are obtained, I.R. bands at 3450, 1738, 1720, 1460, 1370, 1250, 1175, 1030 $cm^{-1}$.

b. starting from XVIII 21 gr of the compound XVII dissolved in 99 ml of ethanol 99% are refluxed 6 hours with 7.39 ml of $H_2SO_4$. The solvent is removed in vacuo, 308 ml of water are added, the product is extracted with $CHCl_3$; the organic phase is washed with $NaHCO_3$ 5% in water, with water and the solvent is removed in vacuo: 16 gr of the compound XX are obtained, which is distilled at 0.11 mm at 220° C giving 11 gr, I.R. bands at 3450, 1738, 1720, 1460, 1370, 1250, 1175, 1030 $cm^{-1}$.

EXAMPLE 10 : 9-hydroxy-19,20-bis-nor-prostanoic acid diethylamide (XXI)

20 gr of sodium salt of the compound XVIII in 194 ml of anhydrous acetone are treated at −10° with 6.15 ml of ethylchlorocarbonate and after 10 minutes at −15°, with 0.0466 ml of N-methylmorpholine.

The mixture is stirred 1 hour at −15°/−20°, 7.7 ml of diethylamine are added, and the mixture is stirred at −10°/0° for 1 hour.

200 ml of $CHCl_3$ and 106 ml of water are added, the solution is stirred 20 minutes at 0°/+5°. The chloroformic phase is separated, washed with water, with $NaHCO_3$ 10% in water, with water, with HCl 5% in water, and again with water.

The solvent is removed in vacuo: 20 gr of white oil of the compound XXI are obtained, I.R. bands at 3440, 1635 $cm^{-1}$.

EXAMPLE 11 : 9-amino-19,20-bis-nor-prostanoic acid ethyl ester (XXII)

10 gr of ethyl ester (XIX) dissolved in 100 ml of methanol saturated with ammonia gas are treated with 2 gr of $PtO_2$ and hydrogen at 20° C and 1 atmosphere. After absorption of the theoretical amount of hydrogen, the catalyst is removed by filtration, the solvent is removed in vacuo. The residue is distilled at 0.01 mm at 230° : 2 gr of compound XXII are obtained, no U.V. absorption, I.R. bands at 3400, 3100, 1720, 1690, 1670, 1250 $cm^{-1}$, amine titration (with perchloric acid) 98% of the theoretical value.

EXAMPLE 12 : 2(7'-hydroxyheptyl)-3-hexyl cyclopentanol (XXIII)

18 gr of ethyl ester XIX dissolved in 200 ml of anhydrous ether are refluxed with 10 gr of $LiAlH_4$ for 5 hours. At 0° water is added, the suspension is acidified with HCl, the organic phase is separated, washed with water, dried on $Na_2SO_4$ and the solvent removed in vacuo. The residue (15 gr) has I.R. bands at 3400, 3100 $cm^{-1}$ and no carbonyl band between 1800, 1600 $cm^{-1}$.

EXAMPLE 13 :
9-methyl-9-hydroxy-19,20-bis-nor-prostanoic acid ethyl ester (XXIV)

32.4 gr of ethyl ester XIX dissolved in 300 ml of ethyl ester are treated slowly in 1 hour at 0° with a Grignard solution obtained from 15.7 gr of methyl iodide and 2.67 gr of Mg in 100 ml of ether. The mixture is refluxed 5 hours, then decomposed at 0° with 100 ml of $NH_4Cl$ 10% in water.

The organic phase is separated, washed with water, dried on $Na_2SO_4$, and the solvent is removed in vacuo. The residue is distilled at 0.01 mm at 240°: 15 gr, I.R. bands at 3400, 3300, 1740, 1710, 1250 $cm^{-1}$.

I claim:

1. 9-hydroxy-19,20-bis-nor-prostanoic acid sodium salt.

2. 9-hydroxy-19,20-bis-nor-prostanoic acid and the pharmaceutically acceptable salts thereof.

3. The ethyl ester of 9-hydroxy-19,20-bis-nor-prostanoic acid.

4. A pharmaceutical composition having hypolipemic activities, platelet aggregation inhibiting properties, and antiulcerous activities consisting essentially of an active component selected from the group consisting of 9-hydroxy-19,20-bis-nor-prostanoic acid and the pharmaceutically acceptable salts thereof, and a pharmaceutical carrier therefor.

5. A pharmaceutical composition as defined in claim 1 wherein the active component is 9-hydroxy-19,20-bis-nor-prostanoic acid sodium salt.

* * * * *

UNITED STATES PATENT AND TRADEMARK OFFICE
CERTIFICATE OF CORRECTION

PATENT NO. : 4,073,938
DATED : February 14, 1978
INVENTOR(S) : Umberto Valcavi

It is certified that error appears in the above-identified patent and that said Letters Patent are hereby corrected as shown below:

[73] Assignees: Istituto Biochimico Italiano di Loredana Lorenzini S.a.s., Milan, Italy and Dr. Madaus & Co., Cologne, West Germany Signed and Sealed this Fourth Day of July 1978

[SEAL]

Attest:

RUTH C. MASON
*Attesting Officer*

DONALD W. BANNER
*Commissioner of Patents and Trademarks*